United States Patent [19]

Kukolja et al.

[11] 3,994,888

[45] Nov. 30, 1976

[54] CEPHALOSPORIN CLEAVAGE PROCESS

[75] Inventors: Stjepan P. Kukolja, Indianapolis; Steven R. Lammert, Greenwood, both of Ind.

[73] Assignee: Eli Lilly and Company, Indianapolis, Ind.

[22] Filed: June 13, 1975

[21] Appl. No.: 586,688

Related U.S. Application Data

[62] Division of Ser. No. 371,011, June 18, 1973, Pat. No. 3,905,966.

[52] U.S. Cl. ............................. 260/243 C; 424/246
[51] Int. Cl.² ........................................ C07D 501/18
[58] Field of Search ................................ 260/243 C

[56] References Cited
UNITED STATES PATENTS

| | | | |
|---|---|---|---|
| 3,487,070 | 12/1969 | Sheehan | 260/243 C |
| 3,487,074 | 12/1969 | Sheehan | 260/243 C |
| 3,769,281 | 10/1973 | Chauvette | 260/243 C |
| 3,905,966 | 9/1975 | Kukolja et al. | 260/243 C |

Primary Examiner—Nicholas S. Rizzo
Attorney, Agent, or Firm—William C. Martens, Jr.; Everet F. Smith

[57] ABSTRACT

A 7-(amic acid) cephalosporin is cleaved by conversion to the corresponding mixed anhydride and cleavage of the mixed anhydride to the corresponding 7-aminocephalosporin or to a corresponding 7-acylamidocephalosporin.

14 Claims, No Drawings

CEPHALOSPORIN CLEAVAGE PROCESS

This is a division of application Ser. No. 371,011, filed June 18, 1973, now U.S. Pat. No. 3,905,966.

BACKGROUND OF THE INVENTION

This invention relates to a process for selectively cleaving an amic acid function from a 7-(amic acid) cephalosporin.

It has been a customary practice for some time in the development of cephalosporin antibiotics to employ an imide substituent in the 7-position when that portion of the molecule was not the point of investigation. The presence of such a protective group, particularly the phthalimido group, tended to render the 7-position chemically quite inert and afforded the possibility to treat other portions of the molecule rather vigorously with the relative assurance that the 7-position would remain intact.

However, it has long been recognized that the presence of an imide function in the 7-position of a cephalosporin rendered the structure antibiotically only minimally active. Unfortunately, it has been impossible to successfully cleave a 7-imido group from a cephalosporin to liberate the protected amino group. Thus, the investigator was left with a stable substituent in the 7-position, and one which rendered a cephalosporin exhibiting only minimal antibiotic activity. The use of such a substituent thus could be attractive commercially only if it could conveniently be removed at any desired point in a synthetic scheme.

It is not intended by the above to say, in general, that it has been impossible successfully to cleave an imide group. Several methods for accomplishing this are recognized. The Japanese publication by Minoru Shindo, "Cleavage Reactions of the Phthalimido Group," *Yuki Gosei Kagaku Kyokai Shi*, 29 (5), (1971) pp. 496–509, contains an extensive discussion of cleavage techniques. Any of these would be available in achieving cleavage of the imide function from a cephalosporin were this the only essential consideration. However, it is at least of equal importance to employ conditions which will accomplish cleavage without sacrificing the structural integrity of the cephalosporin molecule. To date, this has been impossible to achieve.

It has been possible to achieve a partial cleavage of the imide side chain of a cephalosporin structure to form the corresponding amic acid side chain (see, for example, Sheehan et al., *Journal of the American Chemical Society*, 73, (1951) pp. 4367–4372; Sheehan et al., *Journal of the American Chemical Society*, 78, (1956) pp. 3680–3683; Perron et al., *Journal of Organic Chemistry*, 7, (1964) pp. 483–487). The phthalimide function has been converted to the corresponding phthalamic acid by alkaline hydrolysis such as is described in the first Sheehan publication. However, as noted in the second Sheehan publication, all attempts to carry the cleavage beyond this point have met with failure, the β-lactam ring of the penicillin being preferentially opened with destruction of the penicillin.

Sheehan, U.S. Pat. No. 3,487,074, discloses the cleavage of 6-phthalimido-3-penamyl-carboxylic acid by treatment thereof with hydrazine hydrate in dioxane for 12 hours at room temperature. However, this method has been found to be unsuccessful when applied to penicillins and cephalosporins, although moderate success was experienced when this approach was applied to a 7-phthalimido Δ²-cephalosporin [see Spry, D. O., *Journal of the American Chemical Society*, 92, (1970), p. 5007].

A method has now been discovered by which an amic acid function of a cephalosporin can be cleaved without opening the β-lactam ring. This invention comprises such a method. Normally, the amic acid function will be obtained by partial cleavage of an imide function; however, this is by no means essential.

SUMMARY OF THE INVENTION

A process for cleaving the amic acid function of a 7-(amic acid) cephalosporin having the formula

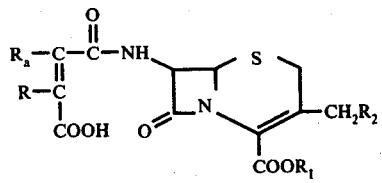

in which R and $R_a$ are hydrogen, or R and $R_a$ taken together with the carbon atoms to which they are attached represent an ortho-phenylene ring;

$R_1$ is a carboxy protecting group; and $R_2$ is hydrogen, acetoxy, methoxy, methylthio, (5-methyl-1,3,4-thiadiazol-2-yl)thio, or (1-methyl-1H-tetrazol-5-yl)thio; which comprises 1. reacting said 7-(amic acid) cephalosporin with an alkyl chloroformate in the presence of a tertiary amine to form the corresponding mixed anhydride having the formula

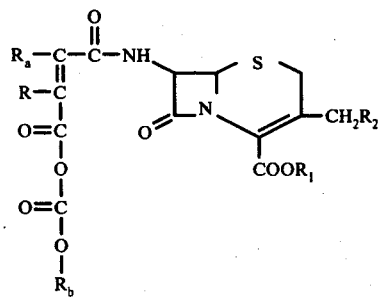

in which
   $R_b$ is an alkyl group having from 1 to 4 carbon atoms;
2. reacting the product mixture from the aforementioned chloroformate treatment with a hydrazine of the formula

in which
   $R_3$ and $R_4$ independently are hydrogen or methyl; and
3. 
   a. reacting the reaction mixture from the aforementioned hydrazine treatment with an acyl halide to produce the corresponding 7-acylamido cephalosporin; or
   b. when at least one of $R_3$ and $R_4$ is methyl, recovering the corresponding 7-amino cephalosporin from the reaction mixture of the aforementioned hydrazine treatment; or c. when R and R₄ are hydrogen, heating the reaction mixture from the aforementioned hydrazine treatment to a temperature of from about 50° C. to about 100° C. to produce the corresponding 7-amino cephalosporin; or d. when R₃ and R₄ are hydrogen, reacting the reaction mixture from the aforementioned hydrazine treatment with acid to produce the corresponding 7-amino cephalosporin in the form of its acid addition salt.

DETAILED DESCRIPTION OF THE INVENTION

Unless otherwise specifically mentioned, as used herein, the terms "cleavage", "cleaving", and the like, are intended to refer to the removal of a substituent in the 7-position of a cephalosporin thereby to produce a free 7-amino cephalosporin, a free 7-amino cephalosporin in the form of its acid addition salt, or a 7-amino cephalosporin resulting from removal of the amic acid function followed by re-acylation to contain another acyl substituent in its 7-position.

In accordance with one aspect of the process of this invention, a first step involves conversion of an amic acid function to produce a corresponding mixed anhydride. When, in the amic acid structure, R and R$_a$ taken together with the carbon atoms to which they are attached represent an ortho phenylene ring, the source of the amic acid generally will be a phthalimido compound which has been partially cleaved by recognized techniques. The structure of the resulting phthalamic acid is as follows:

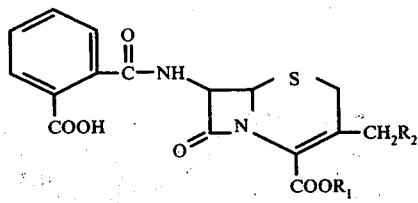

The preparation of a compound having the above structure from the corresponding phthalimido compound is well-recognized in the art, and any of the known conditions can be employed. A typical method by which partial cleavage is effected involves an alkaline hydrolysis such as is described in Sheehan et al., *Journal of the American Chemical Society*, 73, (1951), pp. 4367–4372.

The conditions of alkaline hydrolysis which can be employed to accomplish partial cleavage to the amic acid include use of an alkali metal hydroxide or sulfide, such as sodium hydroxide, potassium hydroxide, lithium hydroxide, sodium sulfide, potassium sulfide, lithium sulfide, and the like. Generally, from about 1 to about 2 equivalents of the alkali metal hydroxide or sulfide are employed, except in the instance in which the free acid of the cephalosporin is employed, in which case the free carboxyl itself will consume one equivalent of the alkaline reagent, and, therefore, an additional equivalent will be required.

In general, the pH of the reaction medium ranges from about 9 to about 11. The hydrolysis is achieved generally by use of an aqueous medium containing an inert, water-miscible organic solvent, such as, for example, tetrahydrofuran, N,N-dimethylformamide, acetone, dimethylsulfoxide, dioxane, and the like.

The partial cleavage generally is quite rapid, typically being completed in from about 3 to about 30 minutes, and more typically in from about 5 to about 10 minutes. The temperature of reaction usually is from about −10° C. to about room temperature, and preferably, about 0° C.

The amic acid can also have the formula

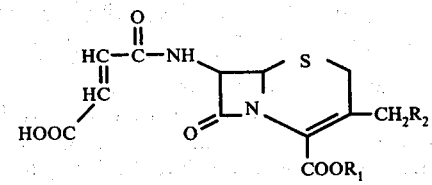

The above amic acid, as well as phthalamic acid defined herein, are also available from sources other than their corresponding imide precursors. For example, the free amino compound can be reacted with the appropriate anhydride, for example, maleic anhydride, to produce the corresponding amic acid compound, specifically, in this case, the 3-carboxyacrylamido compound.

One step of the process of this invention comprises the conversion of the amic acid to a mixed anhydride. The mixed anhydride is not isolated in accordance with the process of this invention; however, it has the formula

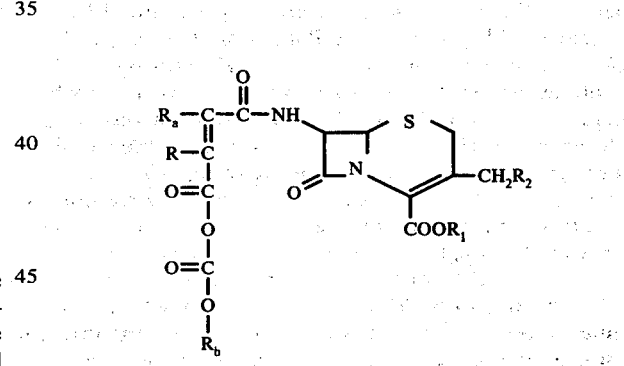

R$_b$ represents an alkyl group, preferably a lower alkyl group having from 1 to 4 carbon atoms.

The conversion of the amic acid to the mixed anhydride is accomplished by reacting the amic acid with an alkyl chloroformate, such as ethyl chloroformate, propyl chloroformate t-butyl chloroformate, isobutyl chloroformate, and the like. Preferably, a lower alkyl chloroformate is employed, typically one in which the alkyl group has from about 1 to about 4 carbon atoms. This reaction is carried out in the presence of a tertiary amine, such as pyridine, quinoline, triethylamine, N-methylmorpholine, N,N-dimethylaniline, and the like. Additionally, this reaction typically is carried out in the presence of an aprotic organic solvent, that is, one which does not offer or accept protons. A wide variety of such solvents are known to those skilled in the art and can be used in accordance with the process of this invention. Included as such solvents are N,N-dimethylformamide, N,N-dimethylacetamide, tetrahydrofuran, dioxane, aliphatic nitriles, such as acetonitrile, propionitrile, and the like; aromatic hydrocarbons and halogenated derivatives, such as benzene, toluene, dichlorobenzene, and the like; and aliphatic halogenated hydrocarbons, such as methylene chloride, chloroform, bromoform, carbon tetrachloride, carbon tetrabromide, ethylene dichloride, ethylene dibromide, and the like.

No more than one equivalent of the amide based upon the amic acid is employed, and it is highly preferred to employ a slightly deficient quantity of the amine. Any excess tertiary amine will tend to convert the amic acid to an imide, typically what may have been the original starting material in the process of this invention. A slight excess of the chloroformate can be employed; however, this is not preferred, since any excess will react with the hydrazine employed in the next step of the process of this invention.

The reaction is carried out for from about 5 to about 40 minutes, preferably from about 20 to about 30 minutes at a temperature of from about −20° C. to about +5° C., and preferably from about −20° C. to about −5° C. The mixed anhydride is maintained intact by retaining the reaction mixture at approximately the temperature at which the reaction was carried out.

The aforementioned mixed anhydride cephalosporin can then be selectively cleaved by a step-wise treatment thereof with a hydrazine, typically unsubstituted hydrazine, methyl hydrazine, or N,N'-dimethylhydrazine, followed by product recovery and/or further treatment depending upon the product which is desired and the particular hydrazine which is employed.

The hydrazine treatment involves the reaction of the mixed anhydride in an inert organic solvent such as any of the aprotic solvents mentioned hereinabove with one equivalent of the hydrazine. Care must be taken to avoid the presence of any excess hydrazine. Therefore, in order to ensure the avoidance of such excess, up to one equivalent of the hydrazine per equivalent of the original amic acid is employed, and, typically, a slight deficiency of hydrazine is employed. The reaction is carried out at relatively cold temperatures ranging from about −10° C. to about room temperature and preferably at about ice temperature (0° C.). The hydrazine typically is added to the mixed anhydride mixture while the mixture is at the relatively cold reaction temperature. Thus, the mixture of the mixed anhydride in the organic solvent is maintained at the temperature of reaction while the hydrazine, previously cooled, is added. The reaction is rather rapid, generally being completed within from about 1 to about 10 minutes, and the reaction generally is permitted to proceed for about an additional 5 minutes.

The particular treatment which the hydrazine reaction mixture then receives depends upon the structure of the hydrazine which is employed and the ultimate product which is desired.

The hydrazines which are used have the structure

R$_3$HNNHR$_4$ in which R$_3$ and R$_4$ independently are hydrogen or methyl. When either or both of R$_3$ and R$_4$ are methyl, no further treatment is necessary since the free 7-amino cephalosporin is generated and can be isolated simply by applying techniques well recognized in the art.

When R$_3$ and R$_4$ in the hydrazine which is employed are both hydrogen, a complex of the free 7-amino cephalosporin and the by-product, diketophthalazine, forms, and this complex must be broken. This can be accomplished by heating the mixture or by treating the mixture with acid or, more readily, by a combination of both heat and acid treatment.

When heat is employed, the complex typically can be broken by subjecting the reaction mixture to a temperature of from about 50° C. to about 100° C. for from about 5 to about 20 minutes, and the free amino compound recovered by recognized techniques.

The diketophthalazine complex can also be broken by treating the reaction mixture with an acid. Virtually any acid, organic or inorganic, can be used. Typical such acids include, for example, hydrochloric acid, hydrobromic acid, phosphoric acid, p-toluenesulfonic acid, sulfuric acid, methanesulfonic acid, and the like. An equivalent or a moderate excess of the acid, typically up to about two equivalents of the acid, based upon the amic acid, is employed. Preferably, acid is employed in conjunction with heat, and, therefore, the resulting reaction mixture is heated to a temperature of from about 50° C. to about 100° C., and the decomposition of the complex is permitted to proceed. Depending upon the relative temperature which is employed, the reaction typically will be completed within from about 5 to about 10 minutes. When an acid is employed, the free 7-amino cephalosporin in the form of its acid addition salt is thereby produced and is recovered in accordance with known techniques.

It is also possible to form a 7-acylamido cephalosporin by subjecting the hydrazine reaction mixture to treatment with an acyl halide which contains an acyl function which, in combination with the 7-amino cephalosporin, will form the desired acylamido function. The use of an acyl halide obviates any necessity for heat or acid treatment to decompose the diketophthalazine complex, should such have formed, since the acyl halide itself is sufficiently acidic to accomplish the necessary decomposition. Any of the typical acyl functions can be thereby introduced into the 7-position of the cephalosporin molecule simply by selection of the appropriate acyl halide, preferably the corresponding acyl chloride. The resulting 7-acylamido cephalosporin can be readily recovered by techniques well recognized in the art.

Typical acyl halides, each of which can be employed to produce the ultimate 7-acylamido product, are those of the formula R$_x$—Y in which Y is a halogen, such as chlorine, bromine, or iodine, and R$_x$ is
C$_1$ to C$_8$-alkanoyl;
C$_2$ to C$_8$-chloro- or bromoalkanoyl;
azidoacetyl;
cyanoacetyl;
2-sydnone-3-C$_1$ to C$_3$-alkanoyl;

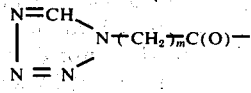

in which
*m* is zero, 1, or 2;

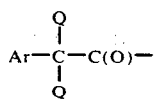

in which each Q is hydrogen or methyl, and Ar is 2-thienyl, 3-thienyl, 2-furyl, 3-furyl, 2-pyrrolyl, 3-pyrrolyl, phenyl, or phenyl substituted with chlorine, bromine, iodine, fluorine, trifluoromethyl, hydroxy, $C_1$ to $C_3$-alkyl, $C_1$ to $C_3$-alkyloxy, cyano, or nitro;

Ar—X—$CH_2$—C(O)— in which X is oxygen or sulfur, and Ar is as defined above; or Ar is 4-pyridyl and X is sulfur; or

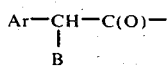

in which Ar is as defined above, and B is —$NH_2$; an amino group protected with benzyloxycarbonyl, $C_1$ to $C_4$-alkoxycarbonyl, cyclopentyloxycarbonyl, cyclohexyloxycarbonyl, benzhydryloxycarbonyl, triphenylmethyl, 2,2,2-trichloroethoxycarbonyl,

or the enamine from methyl acetoacetate or acetylacetone; —OH, or —OH protected by esterification with a $C_1$ to $C_6$-alkanoic acid; —COOH, or —COOH protected by esterification with a $C_1$ to $C_6$-alkanol; —$N_3$; —CN; or —C(O)$NH_2$.

The cephalosporin used as starting material in the process of this invention has the following formula:

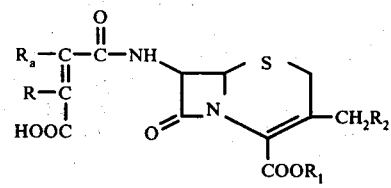

$R_1$ in the above formula as well as in the various products of the process of this invention denotes a carboxy protecting group. The nature of the carboxy protecting group is not important, and any of those recognized in the art can be used. Preferably, however, this group is the residue of an ester function which is removable by acid treatment or by hydrogenation. Preferred carboxy protecting groups include, for example, $C_1$-$C_4$ alkyl, 2,2,2-trihaloethyl, benzyl, p-nitrobenzyl, p-methoxybenzyl, benzhydryl, $C_2$ to $C_6$-alkanoyloxymethyl, phenacyl, or p-halophenacyl, in any of the above of which halo denotes chlorine, bromine, or iodine. Specific illustrations of the preferred ester residues of the carboxyl group of the 7-imido cephalosporin compound used in the process of this invention include, for example, methyl, ethyl, n-propyl, isopropyl, n-butyl, sec-butyl, isobutyl, t-butyl, 2,2,2-trichloroethyl, 2,2,2-tribromoethyl, p-nitrobenzyl, benzyl, p-methoxybenzyl, benzhydryl, acetoxymethyl, pivaloyloxymethyl, propionoxymethyl, phenacyl, p-chlorophenacyl, p-bromophenacyl, and the like.

Highly preferred ester residues are t-butyl, benzyl, p-nitrobenzyl, p-methoxybenzyl, benzhydryl, and 2,2,2-trichloroethyl; most preferably, the ester residue is p-nitrobenzyl.

In the above formula, the 7-position of the cephalosporin contains a 2-carboxybenzamido group (typically derived from a phthalimido group) or a maleamido group.

Thus, the process of this invention proceeds stepwise from a 7-(2-carboxybenzamido)- to an unisolated mixed anhydride to a 7-amino- or 7-acylamido- cephalosporin.

It is also possible to begin the process of this invention with a maleamido cephalosporin. This step-wise sequence includes conversion of 7-maleamido- to an unisolated mixed anhydride to a 7-amino- or 7-acylamido- cephalosporin.

The nature of the substituent in the 3-position of the 7-imido or 7-(amic acid) cephalosporin starting material is not critical, and any of the recognized substituents can be present. Preferably, however, the 3-position will contain one of the following: methyl, acetoxymethyl, methoxymethyl, methylthiomethyl, (5-methyl-1,3,4-thiadiazol-2-yl)thiomethyl, or (1-methyl-1H-tetrazol-5-yl)thiomethyl. The substituent which is present in the 3-position of the cephalosporin starting material will remain intact throughout the sequence of the process of this invention.

The following are representative of the product conversions which are available in accordance with the process of this invention. It will be understood, however, that the ratio of products may vary depending upon the particular reactants which are employed, the relative quantities of reactants, and the conditions of reaction.

Methyl 7-(2-carboxybenzamido)-3-methyl-3-cephem-4-carboxylate to methyl 7-amino-3-methyl-3-cephem-4-carboxylate.

2,2,2-Trichloroethyl 7-(2-carboxybenzamido)-3-acetoxymethyl-3-cephem-4-carboxylate to 2,2,2-trichloroethyl 7-amino-3-acetoxymethyl-3-cephem-4-carboxylate.

p-Nitrobenzyl 7-(2-carboxybenzamido)-3-methoxymethyl-3-cephem-4-carboxylate to p-nitrobenzyl 7-amino-3-methoxymethyl-3-cephem-4-carboxylate.

Benzyl 7-(2-carboxybenzamido)-3-methylthiomethyl-3-cephem-4-carboxylate to benzyl 7-amino-3-methylthiomethyl-3-cephem-4-carboxylate.

Benzhydryl 7-(2-carboxybenzamido)-3-(5-methyl-1,3,4-thiadiazol-2-yl)thiomethyl-3-cephem-4-carboxylate to benzhydryl 7-amino-3-(5-methyl-1,3,4-thiadiazol-2-yl)thiomethyl-3-cephem-4-carboxylate.

t-Butyl 7-(2-carboxybenzamido)-3-(1-methyl-1H-tetrazol-5-yl)thiomethyl-3-cephem-4-carboxylate to t-butyl 7-amino-3-(1-methyl-1H-tetrazol-5-yl)thiomethyl-3-cephem-4-carboxylate.

p-Nitrobenzyl 7-(2-carboxybenzamido)-3-acetoxymethyl-3-cephem-4-carboxylate to p-nitrobenzyl 7-amino-3-acetoxymethyl-3-cephem-4-carboxylate.

p-Nitrobenzyl 7-(2-carboxybenzamido)-3-methyl-3-cephem-4-carboxylate to p-nitrobenzyl 7-amino-3-methyl-3-cephem-4-carboxylate.

p-Nitrobenzyl 7-(2-carboxybenzamido)-3-methylthiomethyl-3-cephem-4-carboxylate to p-nitrobenzyl 7-amino-3-methylthiomethyl-3-cephem-4-carboxylate.

p-Nitrobenzyl 7-(2-carboxybenzamido)-3-(5-methyl-1,3,4-thiadiazol-2-yl)thiomethyl-3-cephem-4-carboxylate to p-nitrobenzyl 7-amino-3-(5-methyl-1,3,4-thiadiazol-2-yl)thiomethyl-3-cephem-4-carboxylate.

p-Nitrobenzyl 7-(2-carboxybenzamido)-3-(1-methyl-1H-tetrazol-5-yl)thiomethyl-3-cephem-4-carboxylate to p-nitrobenzyl 7-amino-3-(1-methyl-1H-tetrazol-5-yl)thiomethyl-3-cephem-4-carboxylate.

p-Methoxybenzyl 7-(2-carboxybenzamido)-3-acetoxymethyl-3-cephem-4-carboxylate to p-methoxybenzyl 7-amino-3-acetoxymethyl-3-cephem-4-carboxylate.

p-Nitrobenzyl 7-maleamido-3-methyl-3-cephem-4-carboxylate to p-nitrobenzyl 7-amino-3-methyl-3-cephem-4-carboxylate.

2,2,2-Trichloroethyl 7-maleamido-3-(1-methyl-1H-tetrazol-5-yl)thiomethyl-3-cephem-4-carboxylate to 2,2,2-trichloroethyl 7-amino-3-(1-methyl-1H-tetrazol-5-yl)thiomethyl-3-cephem-4-carboxylate.

Benzyl 7-maleamido-3-(5-methyl-1,3,4-thiadiazol-2-yl)thiomethyl-3-cephem-4-carboxylate to benzyl 7-amino-3-(5-methyl-1,3,4-thiadiazol-2-yl)thiomethyl-3-cephem-4-carboxylate.

Pivaloyloxymethyl 7-(2-carboxybenzamido)-3-methylthiomethyl-3-cephem-4-carboxylate to pivaloyloxymethyl 7-amino-3-methylthiomethyl-3-cephem-4-carboxylate.

Acetoxymethyl 7-(2-carboxybenzamido)-3-methoxymethyl-3-cephem-4-carboxylate to acetoxymethyl 7-amino-3-methoxymethyl-3-cephem-4-carboxylate.

Phenacyl 7-(2-carboxybenzamido)-3-methyl-3-cephem-4-carboxylate to phenacyl 7-amino-3-methyl-3-cephem-4-carboxylate.

p-Chlorophenacyl 7-(2-carboxybenzamido)-3-acetoxymethyl-3-cephem-4-carboxylate to p-chlorophenacyl 7-amino-3-acetoxymethyl-3-cephem-4-carboxylate.

t-Butyl 7-(2-carboxybenzamido)-3-methyl-3-cephem-4-carboxylate to t-butyl 7-amino-3-methyl-3-cephem-4-carboxylate.

Benzyl 7-(2-carboxybenzamido)-3-acetoxymethyl-3-cephem-4-carboxylate to benzyl 7-amino-3-acetoxymethyl-3-cephem-4-carboxylate.

p-Methoxybenzyl 7-(2-carboxybenzamido)-3-methoxymethyl-3-cephem-4-carboxylate to p-methoxybenzyl 7-amino-3-methoxymethyl-3-cephem-4-carboxylate.

2,2,2-Trichloroethyl 7-(2-carboxybenzamido)-3-methylthiomethyl-3-cephem-4-carboxylate to 2,2,2-trichloroethyl 7-amino-3-methylthiomethyl-3-cephem-4-carboxylate.

t-Butyl 7-(2-carboxybenzamido)-3-(5-methyl-1,3,4-thiadiazol-2-yl)thiomethyl-3-cephem-4-carboxylate to t-butyl 7-amino-3-(5-methyl-1,3,4-thiadiazol-2-yl)thiomethyl-3-cephem-4-carboxylate.

Benzyl 7-(2-carboxybenzamido)-3-(1-methyl-1H-tetrazol-5-yl)thiomethyl-3-cephem-4-carboxylate to benzyl 7-amino-3-(1-methyl-1H-tetrazol-5-yl)thiomethyl-3-cephem-4-carboxylate.

The final product in the immediately preceding list is presented in the form of the free 7-amino compound. However, in accordance with the process of this invention, when an acid treatment is employed, it will be initially obtained in the form of its acid addition salt. This salt, of course, can be readily converted to the free 7-amino compound by well recognized techniques.

Furthermore, the process conversions illustrated hereinabove do not reflect another aspect of this invention, namely, the possibility to obtain, instead of the free 7-amino compound or the acid addition salt thereof, a corresponding 7-acylamido compound. This product is obtainable by employing an acyl halide, typically the acyl chloride, of the 7-acylamido function intended in the final product. The acyl halide is employed in place of the acid used in the final step of the cleavage process. It has been discovered that by so doing the acyl halide itself is sufficiently acidic to break any intermediate complex which may be present in the reaction mixture from the hydrazine treatment. Concomitantly therewith, the free 7-amino group is acylated to the corresponding 7-acylamido compound.

Any of the well recognized acyl groups can be introduced into the 7-position by appropriate selection of the particular acyl halide. These include, for example, phenylacetyl, phenoxyacetyl, phenylglycyl, 2-thienylacetyl, mandelyl, and the like.

Virtually any acyl halide can be employed. Typical such acyl halides include, for example, acetyl chloride, hexanoyl bromide, chloroacetyl chloride, γ-bromooctanoyl chloride, azidoacetyl bromide, cyanoacetyl chloride, sydnoneacetyl chloride, tetrazoleacetyl chloride, 2-thienylacetyl chloride, 3-thienylacetyl bromide, 2-furylacetyl iodide, 3-furylacetyl chloride, 2-pyrrolylacetyl bromide, 3-pyrrolylacetyl chloride, phenylacetyl chloride, α,α-dimethylphenylacetyl chloride, p-chlorophenylacetyl chloride, m-bromophenylacetyl bromide, p-iodophenylacetyl chloride, p-fluorophenylacetyl chloride, m-trifluoromethylphenylacetyl bromide, p-hydroxyphenylacetyl chloride, p-tolylacetyl bromide, m-methoxyphenylacetyl chloride, p-cyanophenylacetyl chloride, p-nitrophenylacetyl bromide, phenoxyacetyl chloride, phenylthioacetyl chloride, p-hydroxyphenoxyacetyl bromide, 4-pyridylthioacetyl chloride, m-chlorophenoxyacetyl chloride, α-aminophenylacetyl chloride, N-(benzyloxycarbonyl)-α-aminophenylacetyl bromide, N-(methoxycarbonyl)-α-aminophenylacetyl chloride, N-(cyclopentyloxycarbonyl)-α-aminophenylacetyl chloride, N-(cyclohexyloxycarbonyl)-α-aminophenylacetyl chloride, N-(benzhydryloxycarbonyl)-α-aminophenylacetyl bromide, N-(triphenylmethyl)-α-aminophenylacetyl chloride, N-(2,2,2-trichloroethoxycarbonyl)-α-aminophenylacetyl chloride, α-hydroxyphenylacetyl chloride, α-formyloxyphenylacetyl chloride, α-acetoxyphenylacetyl chloride, α-carboxyphenylacetyl chloride, α-methoxycarbonylphenylacetyl chloride, α-(t-butoxycarbonyl)phenylacetyl chloride, α-azidophenylacetyl chloride, α-cyanophenylacetyl chloride, α-carbamoylphenylacetyl chloride, and the like.

The products produced in accordance with the process of this invention can be isolated by employing conventional methods. These can include, for example, chromatographic separation, filtration, recrystallization, and the like.

Since the ultimate product of the process of this invention is an ester, the product can be converted to an active antibiotic by, in addition to appropriate acylation of the 7-amino function, cleavage of the ester function by known techniques. Deesterification can be achieved by treatment of the ester with an acid such as trifluoroacetic acid, hydrochloric acid, and the like, or with zinc and acid, such as formic acid, acetic acid, or hydrochloric acid. It can likewise be accomplished by hydrogenating the ester in the presence of palladium, rhodium, or a compound thereof, in suspension or on a carrier such as barium sulfate, carbon, alumina, or the like.

The following examples are provided to further illustrate this invention. It is not intended that this invention be limited in scope by reason of any of these examples.

Preparation A.

Methyl 7-phthalimido-3-methyl-3-cephem-4-carboxylate.

To a solution of 17.3 g. (0.05 mol.) of 7-phthalimido-3-methyl-3-cephem-4-carboxylic acid in 50 ml. of acetone and 20 ml. of water, 5 g. (0.05 mol.) of $KHCO_3$ were slowly added. The resulting solution was evaporated to dryness, and 38 ml. of DMF and 5 ml. of methyl iodide were added to the residue. The mixture was stirred for 3 hrs. at room temperature. To this mixture were then added 100 g. of ice, and the resulting solid product was filtered. The product was crystallized from a mixture of 100 ml. of 2-propanol and 100 ml. of acetone. Yield: 7.91 of crystals, m.p. 187°–188°; ir $(CHCl_3)$ 1790 and 1735 $cm^{-1}$, nmr $(CDCl_3)$ $\delta$ 2.31 (s, 3, $CH_3$), 3.0 and 3.75 (ABq, 2, J=15 Hz), 3.85 (s, 3, $CH_3$), 5.15 (d, 1, J=4.4 Hz), 5.4 (d, 1, J=4.4 Hz) and 7.73 (m, 4, ArH).

Anal. calcd. for $C_{17}H_{14}N_2O_5S$: C, 56.98; H, 3.94; N, 7.82; S, 8.95. Found: C, 56.75; H, 3.66; N, 7.53; S, 8.89%.

Preparation B.

t-Butyl 7-phthalimido-3-methyl-3-cephem-4-carboxylate.

A mixture of 13.76 g. (40 mmol.) of 7-phthalimido-3-methyl-3-cephem-4-carboxylic acid, 10 ml. of conc. $H_2SO_4$, 100 ml. of dry dioxane and 50 ml. of liquid isobutylene was stirred at room temperature in a sealed pressure bottle and then poured into an excess of ice cold aqueous $NaHCO_3$(44 g.). Extraction of the resulting mixture with ethyl acetate and evaporation of the solvent gave a crude ester which was crystallized from $CHCl_3$. The first crop gave 3.34 g. of crystals, m.p. 189°–191°, and the second crop 1.72 g., m.p. 181°–183°; $[\alpha]_D = 77.7°$ (MeCN); ir $(CHCl_3)$, 1800, 1785, and 1735 $cm^{-1}$; nmr $(CDCl_3)$ $\delta$ 1.55 (s, 9, t-Bu); 2.23 (s, 3, $CH_3$), 3.05 and 3.6 (ABq, 2, J = 16 Hz), 5.1 (d, 1, J = 4.5 Hz), 5.72 (d, 1, J = 4.5 Hz) and 7.8 (m, 4, ArH).

Anal. calcd. for: $C_{20}H_{20}N_2O_5S$:
C, 59.99; H, 5.03; N, 7.00; O, 19.98; S, 8.01. Found: C, 60.27; H, 4.91; N, 7.04; O, 20.06; S, 7.74%.

Preparation C.

t-Butyl 7-phthalimido-3-acetoxymethyl-3-cephem-4-carboxylate and t-butyl 7-(2-carboxybenzamido)-3-acetoxy-3-cephem-4-carboxylate.

A mixture of 3.28 g. (10 mmol.) of t-butyl 7-aminocephalosporanate (7-ACA), 1.5 g. (10 mmol.) of phthalic anhydride and 25 ml. of benzene was refluxed for 2 hrs. using a Dean-Stark water collector. The solution was cooled, washed with $NaHCO_3$ (1.68 g. in 20 ml. of $H_2O$), water, and brine, and then dried. The solvent was evaporated to give 1.22 g. of a neutral product. The product was chromatographed over silica gel using a gradient mixture of benzene and ethyl acetate. Fraction 54–87 gave 330 mg. of the phthalimido compound which was recrystallized from dichloromethane/ether; prisms, m.p. 176°–178°; $[\alpha]_D$ + 43.4° (MeCN); ir $(CHCl_3)$ 1800, 1785 and 1735 $cm^{-1}$; EtOH 260 m$\mu$ ($\epsilon$=10,000); nmr $(CDCl_3)$ $\delta$ 1.55 (s, 9, t-Bu); 2.1 (s, 3, $CH_3$), 3.5 (s, 2, $CH_2$); 4.9 and 5.3 (ABq, 2, J = 14 Hz); 5.1 (d, 1, J = 4.5 Hz); 5.82 (d, 1, J = 4.5 Hz), and 7.82 (m, 4, ArH).

Anal. calcd. for: $C_{22}H_{22}N_2O_7S$: C, 57.63; H, 4.84; N, 6.11; O, 24.43; S, 6.99. Found: C, 57.56; H, 4.60; N, 6.31; O, 24.60; S, 6.90%.

After removal of the neutral product the aqueous portion was acidified to pH 3.6 and the acid mixture was extracted with ethyl acetate. Evaporation of the ethyl acetate gave 2.9 g. of t-butyl 7-(2-carboxybenzamido) cephalosporanate. This material was dissolved in 50 ml. of benzene, 15 mg. of imidazole was added, and the mixture was refluxed for 30 min. using a Dean-Stark water collector. After work up procedure and chromatography, 430 mg. of t-butyl 7-phthalimido cephalosporanate was obtained.

The ratio of products from the condensation of phthalic anhydride and the t-Bu ester of 7-ACA depends upon the particular reaction time. If the mixture were heated for only 15 min., about 160 mg. of the phthalimido compound and about 4.34 g. of the phthalamic acid compound would have been obtained.

Preparation D.

p-Methoxybenzyl 7-phthalimido-3-methyl-3-cephem-4-carboxylate.

To a suspension of 13.4 g. (38 mmol.) of 7-phthalimido-3-methyl-3-cephem-4-carboxylic acid in 20 ml. of dioxane and 10 ml. of water were slowly added 3.8 g. of $KHCO_3$. The solution was evaporated to dryness, and 100 ml. of DMF and 8.8 g. of p-methoxybenzyl bromide were added to the potassium salt residue. The mixture was stirred for 2 hrs. and then poured onto 200 g. of ice. The resulting mixture was extracted twice with ethyl acetate. The extract was washed with water and brine, dried, and the solvent was then evaporated. The residue was recrystallized from ethyl acetate. Yield: 4.1 g. of large crystals, m.p. 118°–121°; second crop 1.8 g.; $[\alpha]_D$ + 41.2° (MeCN); ir $(CHCl_3)$ 1800, 1785, 1745 and 1735 $cm^{-1}$, nmr $(CDCl_3)$ $\delta$ 2.15 (s, 3, $CH_3$); 3.0 and 3.7 (ABq, 2, J = 15 Hz), 3.8 (s, 3, $CH_3$), 5.11 (d, 1, J = 4.5 Hz), 5.28 (s, 2, $CH_2$), 5.75 (d, 1, J = 4.5 Hz), 6.8–7.8 (m, 8).

Anal. calcd. for: $C_{24}H_{20}N_2O_6S$: C, 62.06; H, 4.34; N, 6.03; O, 20.67; S, 6.90. Found: C, 62.15; H, 4.31; N, 6.32; O, 20.88; S, 6.82%.

EXAMPLE 1

Methyl 7-(2-carboxybenzamido)-3-methyl-3-cephem-4-carboxylate.

To a solution of 2.86 g. (8 mmol.) of methyl 7-phthalimido-3-methyl-3-cephem-4-carboxylate in 80 ml. of tetrahydrofuran at 0° C. were added 2.4 g. (10 mmol.) of $Na_2S.9H_2O$ and 32 ml. of ice water. After 7 minutes at 0° C., 10 ml. of 1N HCl were added to the mixture. The volume was reduced in vacuo to about 40 ml., and the resulting aqueous solution was washed with ethyl acetate. The pH of the aqueous layer was adjusted to 4.5 with 1N HCl and then was extracted with ethyl acetae (40 ml.). The ethyl acetate layer was washed with brine (30 ml.), dried over $MgSO_4$, and evaporated to give 1.8 g. of methyl 7-(2-carboxybenzamido)-3-methyl-3-cephem-4-carboxylate as an amorphous colorless solid. Recrystallization from acetone gave an analytical sample; m.p. 182°–184.5° (dec.); ir (KBr) 1786, 1630, 1610 (shoulder) and 1665 cm$^{-1}$; nmr (CDCl$_3$/DMSO$_{d-6}$) 2.08 (s, 3, CH$_3$), 3.12 and 3.52 (ABq, 2, J = 17 Hz), 3.8 (s, 3, CH$_3$ester), 5.06 (d, 1, J = 4.5 Hz), 5.86 (dd, 1, J = 4.5 and J = 8.0 Hz) and 7.4–8.0δ (m, 4, ArH).

Anal. calcd. for C$_{17}$H$_{16}$N$_2$O$_6$S: C, 54.25; H, 4.28; N, 7.44; S, 8.52. Found: C, 53.98; H, 4.18; N, 7.73; S, 8.58.

The pH of the aqueous layer from above was lowered to pH 2.5 with 1N HCl and then was extracted with ethyl acetate (2 × 30 ml.). The ethyl acetate extracts were combined, washed with brine (30 ml.) and dried over MgSO$_4$. The ethyl acetate was evaporated in vacuo during which time a colorless crystalline product crystallized. When the volume had been reduced to ca. 10 ml., the solution was filtered giving 190 mg. (6.5%) of 7-(2-carboxybenzamido)-3-methyl-2-cephem-4-carboxylic acid; m.p. 196–198 (dec.); ir (KBr) 1773, 1700, and 1658 cm$^{-1}$; nmr (DMSO$_{d6}$) 1.88 (s, 3, CH$_3$), 4.64 (s, 1, C$_4$-H), 5.15 (d, 1, J = 4.0 Hz), 5.5 (dd, 1, J = 4.0 and 8.0 Hz), 6.15 (s, 1, C$_2$-H) and 7.4–8.0δ (m, 4, ArH).

Anal. calcd. for C$_{16}$H$_{14}$N$_2$O$_6$S: C, 53.03; H, 3.89; N, 7.73; S, 8.85. Found; C, 52.76; H, 3.85; N, 7.68; S, 8.77.

Evaporation of the filtrate from above gave an additional 600 mg. of methyl 7-(2-carboxybenzamido)-3-methyl-3-cephem-4-carboxylate; total yield—80%.

EXAMPLE 2

Methyl 7-amino-3-methyl-3-cephem-4-carboxylate hydrochloride.

To a suspension of methyl 7-(2-carboxybenzamido)-3-methyl-3-cephem-4-carboxylate (752 mg., 2 mmol) in 35 ml. of tetrahydrofuran at 0° C. was added triethylamine (0.28 ml., 2 mmol.). After 15 minutes, ethyl chloroformate (0.2 ml., 2 mmol.) was added, and then after ½ hour at 0° C., anhydrous hydrazine (0.07 ml., 2.2 mmol.) was added to the reaction mixture. After 15 minutes, the mixture was filtered, and the filtrate was evaporated in vacuo to dryness. The crude product was taken up in 20 ml. of chloroform, refluxed for 90 minutes, and then allowed to stir at about 35° C. overnight. Filtration gave 180 mg. of diketophthalazine (m.p. 340°–343°). The filtrate was evaporated to dryness in vacuo. The resulting crude product was taken up in 3 ml. of 1N HCl plus 2 ml. water and washed with ethyl acetate (2 × 7 ml.). Evaporation of the aqueous layer in vacuo gave a yellow amorphous solid which was recrystallized from ethanol/diethyl ether to give 115 mg. of methyl 7-amino-3-methyl-3-cephem-4-carboxylate hydrochloride.

EXAMPLE 3 t-Butyl 7-(2-carboxybenzamido)-3-acetoxymethyl-3-cephem-4-carboxylate.

A solution of 458 mg. (1 mmol.) of t-butyl 7-phthalimido-3-acetoxymethyl-3-cephem-4-carboxylate in 10 ml. of THF was cooled in an ice water bath, and 1.1 ml. of 1N NaOH were then added. After stirring for 5 min., 10 ml. of water and 30 ml. of ethyl acetate were added. The ethyl acetate layer was separated, and 70 mg. of starting material were recovered therefrom. The aqueous layer was acidified to pH 4.0, and the acidified layer was extracted with ethyl acetate. After workup, 330 mg. (83%) of the desired phthalamic acid were obtained [α] + 26.37 (MeCN); EtOH 260 mμ (ε 8800)$^D$; ir (CHCl$_3$) 1785, 1730 and 1685 cm$^{-1}$; nmr (CDCl$_3$) δ 1.55 (s, 9, t-Bu), 2.05 (s, 3, Ac), 3.3 and 3.6 (ABq, 2, J = 17 Hz), 4.72 and 5.2 (ABq, 2, J = 14 Hz), 4.98 (d, 1, J = 4.5 Hz), 5.9 (dd, 1, J = 4.5 and 9 Hz), and 7.5–8 (m, 4, ArH).

EXAMPLE 4 t-Butyl 7-amino-3-acetoxymethyl-3-cephem-4-carboxylate.

In accordance with the procedure of Example 2, t-butyl 7-(2-carboxybenzamido)-3-acetoxymethyl-3-cephem-4-carboxylate is converted to t-butyl 7-amino-3-acetoxymethyl-3-cephem-4-carboxylate hydrochloride, which is converted to the free amine by treatment with NaHCO$_3$ and extraction with chloroform. M.p., ir and nmr spectra are in agreement with an authentic sample prepared according to the method of R. J. Stedman, J. Med. Chem., (1966) p. 444.

EXAMPLE 5 t-Butyl 7-(2-carboxybenzamido)-3-methyl-3-cephem-4-carboxylate.

A solution of 800 mg. (2 mmol.) of t-butyl 7-phthalimido-3-methyl-3-cephem-4-carboxylate in 25 ml. of tetrahydrofuran and 8 ml. of water was cooled in an ice bath. To the solution 660 mg. of Na$_2$S.9H$_2$O were added, and the mixture was stirred and cooled for 10 min. At the end of this period 10 ml. of water were added, and the mixture was extracted with 40 ml. of ethyl acetate. The extract was discarded. The aqueous portion was acidified to pH 4.3 with 1N H$_2$SO$_4$ and then extracted with ethyl acetate. The ethyl acetate extract was dried and evaporated, giving 700 mg. of the title compound. The product was recrystallized from chloroform/cyclohexane; m.p. 178°–179°; ir (nujol) 1770, 1735, and 1680 cm$^{-1}$; nmr (CDCl$_3$+ DMSO$_{d6}$) δ 1.5 (s, 9, t-Bu), 2.1 (s, 3, CH$_3$), 3.2 and 3.5 (ABq, 2, J = 18 Hz), 5.02 (d, 1, J = 4.5 Hz), 5.82 (dd, 1, J = 4.5 and 9Hz), and 7.4–8 (m, H, ArH).

Anal. calcd. for C$_{20}$H$_{22}$N$_2$O$_6$S: C, 57.40; H, 5.30; N, 6.69; O, 22.94 and S, 7.66. Found: C, 57.70; H, 5.20; N, 6.52; O, 22.72 and S, 7.53%.

The identical (nmr, ir, m.p.) substance also can be obtained in 94% yield from phthalic anhydride and the t-butyl ester of 7-ADCA.

EXAMPLE 6 t-Butyl 7-amino-3-methyl-3-cephem-4-carboxylate.

In accordance with the procedure of Example 2, t-butyl 7-(2-carboxybenzamido)-3-methyl-3-cephem-4-carboxylate is converted to t-butyl 7-amino-3-methyl-3-cephem-4-carboxylate hydrochloride. The hydrochloride salt is converted to the free amino este, a colorless solid, using ethyl acetate and sodium bicarbonate.

EXAMPLE 7 p-Methoxybenzyl 7-(2-carboxybenzamido)-3-methyl-3-cephem-4-carboxylate.

A solution of 930 mg. (2 mmol.) of p-methoxybenzyl 7-phthalimido-3-methyl-3-cephem-4-carboxylate in 25 ml. of THF and 8 ml. of water was cooled in an ice water bath, and 660 mg. of $Na_2S.9H_2O$ were then added. The mixture was stirred for 15 min., and 10 ml. of water and 40 ml. of ethyl acetate were added. The layers were separated, and 140 mg. of a neutral material were obtained from the ethyl acetate layer. The aqueous layer was acidified to pH 4.3 with 1N $H_2SO_4$ and extracted twice with ethyl acetate. The ethyl acetate extract was washed, dried, and evaporated to give 660 mg. (68%) of the phthalamic acid as an amorphous solid, $[\alpha]_D$ + 85.6° (MeCN); ir ($CHCl_3$), 1781, 1740 and 1710 $cm^{-1}$, nmr ($CDCl_3$) $\delta$ 2.08 (s, 3, $CH_3$), 3.1 and 3.43 (ABq, 2, J = 17 Hz), 3.79 (s, 3, $CH_3$), 5.0 (d, 1, J = 4.5 Hz), 5.1 (s, 2, $CH_2$), 5.8 (dd, 1, J = 4.5 Hz), 6.75–7.6 (m, 8).

Anal. calcd. for $C_{24}H_{22}N_2O_7S$: C, 59.74; H, 4.60; N, 5.81; O, 23.21; S, 6.65. Found: C, 59.81; H, 4.32; N, 6.07; O, 23.34; S, 6.51%.

EXAMPLE 8 p-Methoxybenzyl 7-amino-3-methyl-3-cephem-4-carboxylate, p-toluene sulfonic acid salt.

In accordance with the procedure of Example 2, p-methoxybenzyl 7-(2-carboxybenzamido)-3-methyl-3-cephem-4-carboxylate is converted to p-methoxybenzyl 7-amino-3-methyl-3-cephem-4-carboxylate, p-toluenesulfonic acid salt, using p-toluenesulfonic acid monohydrate, instead of hydrochloric acid as in Example 2. This material is identical with the salt described by Chauvette et. al., J. Org. Chem., 36, 1265 (1971).

EXAMPLE 9 p-Nitrobenzyl 7-(2-carboxybenzamido)-3-methyl-3-cephem-4-carboxylate.

To an ice cooled solution of 480 mg. (1 mmol.) of p-nitrobenzyl 7-phthalimido-3-methyl-3-cephem-4-carboxylate in 25 ml. of tetrahydrofuran and 5 ml. of water are added 340 mg. of sodium sulfide ($Na_2S.9H_2O$). The mixture was stirred at pH 11.5 for 7 min., and 40 ml. of ethyl acetate and 10 ml. of water were added. The layers were separated, and the organic layer was washed with 5 ml. of water and 5 ml. of brine to give 150 mg. of a neutral material. The aqueous layer was acidified to pH 4.5 with 1N sulfuric acid, and the resulting emulsion was extracted with 25 ml. of ethyl acetate. The extract was washed with brine, dried and evaporated to dryness to give 290 mg. of the crude product, from which 150 mg. (30%) of pure product was obtained.

The same compound also can be prepared by the alternate procedure of refluxing phthalic anhydride and the p-nitrobenzyl ester of 7-ADCA in acetonitrile for 30 min.

A sample was recrystallized from dioxane/water, and colorless crystals were obtained melting at 192°–193°; nmr (DMSO-$d_6$) $\delta$ 2.04 (s, 3, $CH_3$), 3.35 and 3.68 (ABq, 2, J = 18 Hz), 5.2 (d, 1, J = 4 Hz, H-6), 5.4 (s, 2, $CH_2$), 5.8 (d, d, 1, J = 4.5 and 9 Hz), 8 (m, 8 ArH).

Anal. calcd. for $C_{23}H_{19}N_3O_8S$: C, 55.53; H, 3.85; N, 8.45; O, 25.73; S, 6.45. Found: C, 55.67; H, 3.94; N, 8.49; O, 25.89; S, 6.47%.

The subsequent acidification of the aqueous solution to pH 2.0 followed by ethyl acetate extraction produced 120 mg. of p-nitrobenzyl 7-(2-carboxybenzamido)-3-methyl-2-cephem-4-carboxylate.

EXAMPLE 10 p-Nitrobenzyl 7-amino-3-methyl-3-cephem-4-carboxylate, p-toluene sulfonate salt.

A solution of 1.0 g. (2 mmol.) of p-nitrobenzyl 7-(2-carboxybenzamido)-3-methyl-3-cephem-4-carboxylate in 30 ml. of dry tetrahydrofuran was cooled in an ice-salt bath, and 0.28 ml. (2 mmol.) of triethylamine and 0.20 ml. (2 mmol.) of ethyl chloroformate were added. After cooling and stirring for 20 min., 0.15 ml. of 85% hydrazine hydrate was added, and stirring was continued for 10 min. The $Et_3N.HCl$ salt was filtered, and the filtrate was evaporated to dryness. The residue was dissolved in a mixture of 25 ml. of ethyl acetate and 10 ml. of water. The organic extract was separated from the aqueous and washed with $NaHCO_3$ solution, water and brine. After drying, the solvent was evaporated. The residue was dissolved in 10 ml. of acetonitrile, and the solution was refluxed for 50 min. and then cooled. To this solution 380 mg. of p-toluenesulfonic acid hydrate and 2.5 ml. of water were added, the precipitate (160 mg.) was filtered, and most of the acetonitrile was evaporated from the filtrate. Upon cooling and scratching, crystallization began. Two hours later 680 mg. (63%) of the title compound were collected. The purity of product was tested by thin-layer chromatography (tlc) using silica plate and MeOH:Benzene (1:3) system. A sample was recrystallized from methanol-ether, m.p. 170°–174° dec., nmr (DMSO$_{3-6}$) $\delta$2.20 (s,3,$CH_3$), 2.30 (s,3,$CH_3$), 3.6 (s,2,$SCH_2$), 5.22 (s,2,$CH_2$ ester), 5.4 (s,2,azetidinone H's), and 7.1–8.25 (m,8 ArH's); ir (KBr) 1780 (azetidinone CO) and 1730 $cm^{-1}$ ester CO).

Anal. calcd for: $C_{22}H_{23}N_3O_8S_2$: C, 50.66; H, 4.45; N, 8.06; S, 12.30. Found: C, 51.03; H, 4.27; N, 8.19; S, 11.91%.

EXAMPLE 11 p-Nitrobenzyl 7-phenylacetamido-3-methyl-3-cephem-4-carboxylate.

To a suspension of p-nitrobenzyl 7-(2-carboxybenzamido)-3-methyl-3-cephem-4-carboxylate (462 mg., 1 mmol.) in tetrahydrofuran at 0° C. is added triethylamine (0.14 ml., 1 mmol.). After 15 minutes, ethyl chloroformate (0.1 ml., 2 mmol.) is added, and then after 0.5 hour at 0° C., anhydrous hydrazine (0.03 ml., 1 mmol.) is added to the reaction mixture. After 15 minutes, the mixture is filtered, and the filtrate is evaporated to dryness in vacuo. The residue is taken up in acetone (15 ml.) and tetrahydrofuran (15 ml.), and phenylacetyl chloride (0.13 ml., 1 mmol.) is added. After refluxing for 30 min., the mixture is cooled and evaporated in vacuo to dryness. The produce is taken up in chloroform (50 ml.) and washed successively with 1N HCl (30 ml.), 10% sodium bicarbonate (40 ml.), and brine (40 ml.), dried over $MgSO_4$, and evaporated in vacuo to dryness. The colorless product is slurried with ethyl acetate (12 ml.). Filtration gives p-nitrobenzyl 7-phenylacetamido-3-methyl-3-cephem-4-carboxylate. Recrystallization from ethyl acetate gives an analytical sample: m.p. 227°–230°.

EXAMPLE 12 t-Butyl 7-(2'-carboxy)acrylamido-3-acetoxymethyl-3-cephem-4-carboxylate

A solution of 656 mg. (2 mmol.) of t-butyl 7-amino-3-acetoxymethyl-3-cephem-4-carboxylate and 196 mg. (2 mmol.) of maleic anhydride in 20 ml. benzene was refluxed for ½ hour, cooled, and evaporated in vacuo to dryness. Tlc indicated no starting material and one slow moving product: nmr (CDCl$_3$) 94 (s, 9, t-Bu), 127 (s, 3, OAc), 207 and 216 (ABq, J=20 Hz), 293 and 307 (ABq, J=14.0, CH$_2$OAc), 305 (1, d, J=4.5, azetidinone H), 350 (1, q, J=4.5 and 8.0 Hz, azetidinone H), 390 (2H, q, J=12 and 2.0 Hz), 534 (1, d, J=8.0, NH), and 806 Hz (1, broad s, COOH).

EXAMPLE 13 t-Butyl 7-amino-3-acetoxymethyl-3-cephem-4-carboxylate.

In accordance with the procedure of Example 2, t-butyl 7-(3'-carboxy)acrylamido-3-acetoxymethyl-3-cephem-4-carboxylate is converted to t-butyl 7-amino-3-acetoxymethyl-3-cephem-4-carboxylate hydrochloride. The hydrochloride-containing reaction mixture is treated with ethyl acetate and NaHCO$_3$ to obtain a tan colored amorphous product. Nmr and tlc data shows the product to be identical to authentic t-butyl 7-amino-3-acetoxymethyl-3-cephem-4-carboxylate.

EXAMPLE 14

Benzhydryl 7-(2-carboxybenzamido)-3-(5-methyl-1,3,4-thiadiazol-2-yl)thiomethyl-3-cephem-4-carboxylate.

A solution of benzhydryl 7-phthalimido-3-(5-methyl-1,3,4-thiadiazol-2-yl)thiomethyl-3-cephem-4-carboxylate (2 mmol.) in 25 ml. of THF and 8 ml. of water is cooled in an ice-water bath, and 660 mg. of Na$_2$S·9H$_2$O are then added. The mixture is stirred for 15 minutes, and 10 ml. of water and 40 ml. of ethyl acetate are added. The layers are separated, and a neutral material is obtained from the ethyl acetate layer. The aqueous layer is acidified to pH 4.3 with 1N sulfuric acid and is extracted twice with ethyl acetate. The ethyl acetate extract is washed, dried, and evaporated to give the title compound.

EXAMPLE 15

Benzhydryl 7-amino-3-(5-methyl-1,3,4-thiadiazol-2-yl)thiomethyl-3-cephem-4-carboxylate.

A solution of benzhydryl 7-(2-carboxybenzamido)-3-(5-methyl-1,3,4-thiadiazol-2-yl)thiomethyl-3-cephem-4-carboxylate (2 mmol.) in 30 ml. of dry tetrahydrofuran is cooled in an ice-salt bath, and 0.28 ml. (2 mmol.) of triethylamine and 0.20 ml. (2. mmol.) of ethyl chloroformate are added. After cooling and stirring for 20 minutes, 0.106 ml. (2 mmol.) of N-methylhydrazine in 5 ml. of tetrahydrofuran is added. Stirring is continued for about 10 minutes. The Et$_3$N·HCl salt is filtered, and the filtrate is evaporated to dryness. The residue is taken up in about 15 ml. of chloroform, and the mixture is allowed to stand at room temperature for about one hour during which time methylphthalhydrazide (m,p, 243°–245° C.) precipitates. Filtration and evaporation in vacuo of the filtrate gives crude benzhydryl 7-amino-3-(5-methyl-1,3,4-thiadiazol-2-yl)thiomethyl-3-cephem-4-carboxylate.

EXAMPLE 16

2,2,2-Trichloroethyl 7-(2-carboxybenzamido)-3-(1-methyl-1H-tetrazol-5-yl)thiomethyl-3-cephem-4-carboxylate.

In accordance with the procedure of Example 14, 2,2,2-trichloroethyl 7-phthalimido-3-(1-methyl-1H-tetrazol-5-yl)thiomethyl-3-cephem-4-carboxylate is converted to 2,2,2-trichloroethyl 7-(2-carboxybenzamido)-3-(1-methyl-1H-tetrazol-5-yl)thiomethyl-3-cephem-4-carboxylate.

EXAMPLE 17

2,2,2-Trichloroethyl 7-amino-3-(1-methyl-1H-tetrazol-5-yl)thiomethyl-3-cephem-4-carboxylate.

In accordance with the procedure of Example 15, 2,2,2-trichloroethyl 7-(2-carboxybenzamido)-3-(1-methyl-1H-tetrazol-5-yl)thiomethyl-3-cephem-4-carboxylate is converted to 2,2,2-trichloroethyl 7-amino-3-(1-methyl-1H-tetrazol-5-yl)thiomethyl-3-cephem-4-carboxylate with the exception that N,N'-dimethylhydrazine is used instead of N-methylhydrazine.

We claim:

1. A process for cleaving the amic acid function of a 7-(amic acid) cephalosporin having the formula

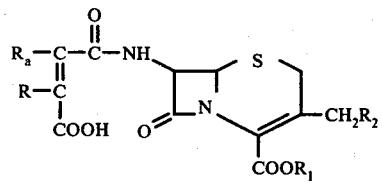

in which
R and R$_a$ are hydrogen, or R and R$_a$ taken together with the carbon atoms to which they are attached represent orthophenylene;
R$_1$ is a carboxy protecting group; and
R$_2$ is hydrogen, acetoxy, methoxy, methylthio, (5-methyl-1,3,4-thiadiazol-2-yl)thio, or (1-methyl-1H-tetrazol-5-yl)thio; which comprises
　1. reacting said 7-(amic acid) cephalosporin with an alkyl chloroformate in the presence of a tertiary amine to form the corresponding mixed anhydride having the formula

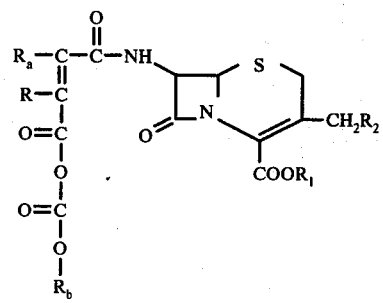

in which
   $R_b$ is an alkyl group having from 1 to 4 carbon atoms;
2. reacting the product mixture from the aforementioned reaction with chloroformate with hydrazine of the formula $H_2NNH_2$;
and
3. producing the corresponding 7-amino cephalosporin by heating the reaction mixture from the aforementioned hydrazine reaction to a temperature of from about 50° C. to about 100° C. or by treating said reaction mixture with acid.

2. Process of claim 1, in which the product mixture from the hydrazine reaction is heated to a temperature of from about 50° C. to about 100° C. to produce the 7-amino cephalosporin.

3. Process of claim 1, in which the product mixture from the hydrazine reaction is reacted with acid to produce the 7-amino cephalosporin in the form of its acid addition salt.

4. Process of claim 1, in which the amic acid cephalosporin is reacted with an alkyl chloroformate in the presence of a tertiary amine at a temperature of from about −20° C. to about +5° C.

5. Process of claim 4, in which the alkyl chloroformate is ethyl chloroformate.

6. Process of claim 3, in which the product mixture from the reaction with chloroformate is first reacted with up to 1 equivalent of a hydrazine in which $R_3$ and $R_4$ are hydrogen per equivalent of the amic acid at a temperature of from about −10° C. to about room temperature for from about 1 to about 10 minutes, and the resulting reaction mixture is reacted with from about 1 to about 2 equivalents of an acid selected from the group consisting of hydrochloric acid, hydrobromic acid, phosphoric acid, p-toluenesulfonic acid, methanesulfonic acid, and sulfuric acid per equivalent of the original amic acid for about 5 to about 10 minutes to produce the corresponding 7-amino cephalosporin in the form of its acid addition salt.

7. Process of claim 1, in which $R_1$ is $C_1$–$C_4$ alkyl, 2,2,2-trichloroethyl, benzyl, p-nitrobenzyl, p-methoxybenzyl, benzhydryl, $C_2$–$C_6$ alkanoyloxymethyl, phenacyl, or p-halophenyacyl.

8. Process of claim 1, in which R and $R_a$ are hydrogen.

9. Process of claim 1, in which R and $R_a$ taken together with the carbon atoms to which they are attached represent ortho-phenylene.

10. Process of claim 1, in which $R_1$ is p-nitrobenzyl.

11. Process of claim 1, in which $R_2$ is hydrogen.

12. Process of claim 1, in which $R_2$ is acetoxy.

13. Process of claim 1, in which $R_2$ is (5-methyl-1,3,4-thiadiazo-2-yl)thio.

14. Process of claim 1, in which $R_2$ is (1-methyl-1H-tetrazol-5-yl)thio.

* * * * *